United States Patent [19]

Hamamoto et al.

[11] Patent Number: 5,728,890
[45] Date of Patent: Mar. 17, 1998

[54] PROCESS FOR PRODUCING A CYCLOALKANOL AND CYCLOALKANONE

[75] Inventors: Toshikazu Hamamoto; Mitsuo Yamanaka; Takato Nakamura; Tetsuro Shimano, all of Ube, Japan

[73] Assignee: Ube Industries, Ltd., Ube, Japan

[21] Appl. No.: 600,981

[22] PCT Filed: Jun. 9, 1995

[86] PCT No.: PCT/JP95/01165

§ 371 Date: Jan. 30, 1996

§ 102(e) Date: Jan. 30, 1996

[87] PCT Pub. No.: WO95/34523

PCT Pub. Date: Dec. 21, 1995

[30] Foreign Application Priority Data

Jun. 10, 1994 [JP] Japan .................... 6-128828

[51] Int. Cl.$^6$ .............. C07C 45/53; C07C 35/08; C07F 15/00; C07F 17/02
[52] U.S. Cl. .............. 568/361; 568/821; 568/835; 568/838; 556/136; 556/137
[58] Field of Search .................. 568/361, 821, 568/835, 838; 556/136, 137

[56] References Cited

U.S. PATENT DOCUMENTS 3,925,316  12/1975  Brunie .
4,482,746  11/1984  Hermolin .
5,120,886  6/1992  Lyons .

*Primary Examiner*—C. Warren Ivy
*Assistant Examiner*—Jean F. Vollano
*Attorney, Agent, or Firm*—Burgess, Ryan & Wayne

[57] ABSTRACT

A cycloalkylhydroperoxide, preferably having a $C_{5-20}$ cycloalkyl group, is decomposed by bringing it into contact with a ruthenium complex of the formula:

$$[RuCl_2L_n]_m \qquad (I)$$

wherein L=a neutral ligand, n=1–4 and m≧1, for example, [RuCl$_2$(PPh$_3$)$_3$], to produce a cycloalkanol and cycloalkanone.

7 Claims, No Drawings

PROCESS FOR PRODUCING A CYCLOALKANOL AND CYCLOALKANONE

TECHNICAL FIELD

This is the national stage application of PCT/JP95/01165 filed Jun. 9, 1995 published as WO95/34523 on Dec. 21, 1995.

The present invention relates to a process for producing a cycloalkanol and cycloalkanone at a high yield by decomposing a cycloalkylhydroperoxide in the presence of a catalyst.

The cycloalkanol and cycloalkanone are compounds very useful as materials for producing polyamide polymers, for example, nylon, as intermediates for synthesizing chemical reagents and as organic solvents.

BACKGROUND ART

As a process for producing a cycloalkanol and cycloalkanone by decomposing a cycloalkylhydroperoxide in the presence of a ruthenium catalyst, the process disclosed in Japanese Unexamined Patent Publication (Kokai) No. 61-167631 wherein chromium and ruthenium compounds soluble in the reaction system are used as a decomposition reaction, catalyst, and the process disclosed in Japanese Unexamined Patent Publication (Kokai) No. 63-156735 wherein a ruthenium compound soluble in the reaction system is used together with an isoindolin derivative as a decomposition reaction catalyst, are known.

However, among the conventional processes, the former process is disadvantageous in that where a soluble ruthenium compound such as ruthenium acetylacetonate or ruthenium carboxylate is used alone, the catalyst is degraded during reaction and converted to a precipitate having a low activity, and particularly in a continuous reaction procedure, the reaction rate is significantly reduced. To solve the above-mentioned problems, the ruthenium compound must be used together with a chromium compound which is toxic and thus difficult to handle, and of which the waste liquid requires a complicated treatment to maintain the catalyst at a soluble state. Also, in the latter conventional process, there is a problem that to the above-mentioned soluble ruthenium compound must be added a ligand consisting of an isoindolin derivative, which is expensive. Further, in these conventional processes there is a further problem that the expensive ruthenium catalyst must be employed at a considerably high concentration.

Furthermore, these conventional process have other disadvantages in that when these processes are carried out industrially, since these processes use a soluble ruthenium catalyst, the catalyst must be recovered by a complicated procedure in which a reaction liquid is withdrawn from the reaction system, portions of the residual materials and reaction products are separated by distillation, and thereafter the catalyst contained in the reaction liquid is recycled and reused. In addition to the above-mentioned disadvantage, the conventional processes have another disadvantage in that during the distillation and recycling of the reaction liquid, the catalyst is inevitably deteriorated or precipitated, and thus lost in a great amount, and the continuous reaction by recycling and reusing of the catalyst in the soluble in an activated condition becomes difficult.

In consideration of the above-mentioned technical background, an object of the present invention is to provide a process for forming a cycloalkanol and cycloalkanone from a cycloalkylhydroperoxide in the presence of a small amount of a ruthenium catalyst insoluble in the reaction system and having a high activity at a high reaction rate at a high yield and at a high selectivity (the percentage of the produced target compound based on the total amount of the reaction products).

DISCLOSURE OF THE INVENTION

The process of the present invention for producing a cycloalkanol and cycloalkanone comprises decomposing a cycloalkylhydroperoxide by bringing it into contact with a ruthenium complex represented by the general formula (I):

$$[RuCl_2L_n]_m$$

in which formula (I), L represents a neutral ligand coordinate-bonded to a ruthenium atom, n represents an integer of 1 to 4, and m represents an integer of 1 or more.

BEST MODE OF CARRYING OUT THE INVENTION

In the process of the present invention, a cycloalkylhydroperoxide is decomposed by contacting with a catalyst consisting of the specific ruthenium complex of the formula (I), to produce a corresponding cycloalkanol and cycloalkanone.

The cycloalkylhydroperoxide usable for the process of the present invention is preferably selected from cycloalkyl hydroperoxide compounds having a cycloalkyl group with 5 to 20 carbon atoms, for example, cyclopentylhydroperoxide, cyclohexylhydroperoxide, cycloheptylhydroperoxide, cyclooctylhydroperoxide, cyclononylhydroperoxide, cyclodecylhydroperoxide, cyclododecylhydroperoxide, cyclopentadecylhydroperoxide, and cyclohexadecylhydroperoxide.

Each of the above-mentioned cycloalkylhydroperoxides can be produced by subjecting a cycloalkane corresponding to the cycloalkylhydroperoxide to a liquid phase catalytic reaction with molecular oxygen, for example, air, in the absence of a substance, for example, a transition metal, which accelerates the decomposition of the cycloalkylhydroperoxide, at a temperature of 120° to 80° C. under a pressure of 1 to 20 atmospheres.

In the process of the present invention, the cycloalkylhydroperoxide, which is isolated by distillation or extraction from the oxidation reaction liquid produced from the cycloalkane by the above-mentioned procedures, may be diluted with a cycloalkane or an aromatic hydrocarbon solvent, for example, benzene or toluene, or a non-refined cycloalkylhydroperoxide-containing mixture liquid (namely, the above-mentioned oxidation reaction liquid) may be used without processing, or concentrated. By using the mixture liquid, the cycloalkylhydroperoxide contained in the liquid can be decomposed at a high efficiency to produce the corresponding cycloalkanol or cycloalkanone by the process of the present invention. In the above-mentioned solution of the cycloalkylhydroperoxide diluted with the solvent, or in the above-mentioned oxidation reaction liquid, usually the content of the cycloalkylhydroperoxide is preferably 0.1 to 20% by weight, more preferably 0.5 to 10% by weight.

Where an oxidation reaction liquid of a cycloalkane is employed, there is an advantage in that in addition to the reaction by which the cycloalkylhydroperoxide contained in the liquid is directly converted to the target compound, another reaction of the residual cycloalkane remaining in the oxidation reaction liquid with the cycloalkylhydroperoxide occurs, to thereby produce the target cycloalkanol and cycloalkane and to further increase the yield of the target compounds. Also, where the above-mentioned oxidation reaction liquid is employed, it is preferable that before decomposing the cycloalkylhydroperoxide, optionally, the oxidation reaction liquid be rinsed with water or an alkali solution to thereby remove acids contained in the liquid. In this case, hydroxides and carbonates of alkali metals and alkaline earth metals, for example, sodium hydroxide, potassium hydroxide, calcium hydroxide, sodium carbonate, potassium carbonate, and calcium carbonate are used to prepare the alkali solution.

The ruthenium compounds represented by the general formula (I) are ruthenium complexes insoluble in the reaction system, for example, the above-mentioned oxidation reaction liquid of cycloalkane.

In the formula (I), the neutral ligand represented by L is preferably selected from neutral ligands capable of coordinate-bonding to a ruthenium atom, for example, tertiary arylphosphine compounds, arene compounds, diene compounds, nitrile compounds, pyridine compounds, 2,2'-bipyridine compounds, 1,10-phenanthroline compounds and dimethylsulfoxide compounds. The term "a neutral ligand" refers to a ligand capable of coordinate-bonding to a central metal atom without changing the formal valence of the central metal atom. In the formula (I), where n is an integer of 2 or more, the two or more neutral ligands represented by L may be the same as or different from each other, as far as the ligands can coordinate-bond to a ruthenium atom to form the above-mentioned ruthenium complex. In the formula (I), m is an integer of 1 or more, usually 1 or 2. The above-mentioned ruthenium complexes are known and almost all of the complexes can be readily synthesized by using ruthenium trichloride as a starting material.

The tertiary arylphosphine compounds for forming the above-mentioned ligands include substituted and unsubstituted tertiary arylphosphine compounds, for example, triphenylphosphine, tris(4-methylphenyl)phosphine, tris(4-chlorophenyl)phosphine, tris(4-fluorophenyl)phosphine and tris(4-methoxyphenyl)phosphine.

The ruthenium complexes containing the above-mentioned tertiary arylphosphine compounds as the ligands L include, for example, dichloro-tris(triphenylphosphine) ruthenium, dichloro-tris(tris(4-methylphenyl)phosphine) ruthenium, dichloro-tris(tris(4-chlorophenyl)phosphine) ruthenium, dichloro-tris(tris(4-fluorophenyl)phosphine) ruthenium, and dichloro-tris(tris(4-methoxyphenyl) phosphine)ruthenium. Among these compounds, dichloro-tris(triphenylphosphine)ruthenium is preferably employed.

The atone compounds usable as the ligands include substituted and unsubstituted arene compounds, for example, benzene, toluene, p-xylene, mesitylene, p-cymene, anisole and cycloheptatriene.

The ruthenium complexes having the ligands consisting of the arene compounds include, for example, tetrachloro-bis(η-benzene)diruthenium, tetrachloro-bis(η-toluene) diruthenium, tetrachloro-bis(η-xylene)diruthenium, tetrachloro-bis(η-mesitylene)diruthenium, tetrachloro-bis (η-p-cymene)diruthenium, tetrachloro-bis(η-anisole) diruthenium, and tetrachloro-bis(η-cycloheptatriene) diruthenium. Among these compounds, tetrachloro-bis(η-benzene)diruthenium and tetrachloro-bis(η-p-cymene) diruthenium are preferably employed.

The diene compounds usable as the ligand L include diene compounds capable of coordinate-bonding, as a divalent ligand, to a ruthenium atom, for example, cyclooctadiene and norbornadiene.

The ruthenium complexes containing, as ligands L, the diene compounds, include associations of dichloro (cyclooctadiene)ruthenium and tetrachloro-bis (norbornadiene)diruthenium. Among these compounds, the associations of dichloro(cycloctadiene)ruthenium are preferably employed. Where cyclooctadiene is used as a ligand, the resultant ruthenium complex is in the form of an association of the formula (I) wherein m is 3 or more.

The nitrile compounds usable as the ligands L include alkylnitrile compounds, for example, acetonitrile, propionitrile and butyronitrile, and arylnitriles, for example, benzonitrile.

The ruthenium complexes having ligands L consisting of the nitrile compounds include dichloro-tetrakis(acetonitrile) ruthenium, dichloro-tetrakis(propionitrile)ruthenium, dichloro-tetrakis(butyronitrile)ruthenium and dichloro-tetrakis(benzonitrile)ruthenium. Among these compounds, dichloro-tetrakis(acetonitrile)ruthenium and dichloro-tetrakis(benzonitrile)ruthenium are preferably employed.

The pyridine compounds 2,2'-bipyridine compounds and 1,10-phenanthroline compounds usable as the ligands L, may be unsubstituted or substituted with at least one substituent consisting of an alkyl group, aryl group or halogen atom, which is attached to a carbon atom located in a position at which the substituent does not hinder coordinate bonding of the resultant ligands to a ruthenium atom, for example, 4-methylpyridine, 4,4'-dimethyl-2,2'-bipyridine and 5-methyl-1,10-phenanthroline.

The ruthenium complexes of the formula (I) having the ligands L consisting of the pyridine compound, 2,2'-bipyridine compounds or 1,10-phenanthroline compounds include, for example, dichloro-tetra(pyridine)ruthenium, dichloro-tris(2,2'-bipyridine)ruthenium, dichloro-tris(4,4'-dimethyl-2,2'-bipyridine)ruthenium and dichloro-tris(1,10-phenanthroline)ruthenium. Among these compounds, dichloro-tetra(pyridine)ruthenium and dichloro-tris(2,2'-bipyridine)ruthenium are preferably employed.

Also, in the formula (I), where n represents 2 to 4, the ruthenium complexes having the ligands different from each other include, for example, dichloro-bis(acetonitrile)bis (triphenylphosphine)ruthenium. Also, the ruthenium complexes having ligands L consisting of dimethylsulfoxide include, for example, dichloro-tetrakis(dimethylsulfoxide) ruthenium.

The decomposition of the cycloalkylhydroperoxide in accordance with the process of the present invention is preferably conducted by adding (for example, dispersing), as a catalyst, the above-mentioned insoluble ruthenium complex in an amount of 0.01 to 250 ppm by weight, more preferably 0.1 to 150 ppm by weight, in terms of ruthenium metal, into the solution containing the cycloalkylhydroperoxide (for example, the oxidation reaction liquid, etc.) and controlling the reaction temperature to 25° to 180° C., more preferably 80° to 160° C. and the reaction pressure to 1 to 30 atmospheres. If the reaction temperature is lower than 25° C., the decomposition rate may be low and if it is higher than 180° C., the yield of the target compounds may become low. Also, even if the concentration of the catalyst is too high, no specific effect is obtained. Therefore, the catalyst is preferably used in the above-mentioned amount.

The decomposition reaction is carried out while generating a heat of reaction, and thus the reaction temperature is preferably controlled appropriately by eliminating the heat of reaction. For this purpose, for example, a reactor equipped with a reflux condenser and a stirrer is preferably employed. In this case, since the ruthenium complex of the formula (I) is insoluble in cycloalkane and the oxidation reaction liquid of cycloalkane, the ruthenium complex can be distributed in the reaction system by using various means, for example, a suspension bed or packing bed.

By decomposing the cycloalkylhydroperoxide by the above-mentioned process, a decomposition reaction liquid of the cycloalkylhydroperoxide, comprising a cycloalkanone, for example, cyclopentanone, cyclohexanone, cycloheptanone, cyclooctanone, cyclononanone, cyclodecanone, cyclododecanone, cyclopentadecanone and cyclohexadecanone, and a cycloalkanol, for example, cyclopentanol, cyclohexanol, cycloheptanol, cyclooctanol, cyclononanol, cyclodecanol, cyclododecanol, cyclopentadecanol, and cyclohexadecanol. The catalyst is removed from the resultant decomposition reaction liquid, for example, by filtering, then, if necessary, the decomposition reaction liquid is rinsed with water or an aqueous alkali solution to remove acids, and the target compounds, namely the cycloalkanone and cycloalkanol are isolated and purified by distilling, etc.

When the oxidation reaction liquid of the cycloalkane is subjected to the decomposition reaction of the process of present invention, non-reacted cycloalkane is collected by distilling and recycled and reused in the oxidation reaction step for the process of the present invention.

EXAMPLES

The present invention will be further explained by the following examples.

In the examples, the conversion of cyclohexylhydroperoxide (CHP) and the total yield (KA yield) of cyclohexanone (K) and cyclohexanol (A) were determined by measuring the amounts of cyclohexylhydroperoxide (CHP), cyclohexanone (K), and cyclohexanol (A) by a gas chromatography and calculating in accordance with the following equations.

$$CHP\ conversion\ (\%) = \frac{CHP\ consumption\ (mole)}{CHP\ charge\ (mole)} \times 100$$

$$KA\ yield\ (\%) = \frac{K\ production\ (mole) + A\ production\ (mole)}{CHP\ consumption\ (mole)} \times 100$$

EXAMPLE 1

[Oxidation of cyclohexane with air]

Cyclohexane in an amount of 300 g was charged in a pressure-resistant glass autoclave equipped with a reflux condenser, a thermometer, a water-separator, a gas-inlet pipe, a stirrer and an outlet for discharging reaction liquid and having an inner volume of 500 ml, and heated while stirring (800 rpm) and flowing a nitrogen gas under a pressure of 10 kg/cm$^2$ at a flow rate of 40 l/hr through the autoclave. When the temperature reached 150° C., the nitrogen gas was replaced by air (pressure: 10 kg/cm$^2$, flow rate: 40 l/hr) to start an oxidation reaction.

At a stage of 260 minutes after the start of the reaction, the resultant oxidation reaction liquid was cooled. The oxidation reaction liquid contained, per g of the oxidation reaction liquid, 0.1399 millimole of cyclohexylhydroperoxide (CHP), 0.0844 millimole of cyclohexanol (A) and 0.1340 millimole of cyclohexanone (K).

[Decomposition of cyclohexylhydroperoxide]

The above-mentioned cyclohexane-oxidation reaction liquid in an amount of 10 g and a catalyst consisting of dichloro-tris(triphenylphosphine)ruthenium [RuCl$_2$(PP$_3$)$_3$] were charged in a pressure-resistant glass autoclave equipped with a reflux condenser, a thermometer, a stirrer and an outlet for withdrawing a reaction liquid and having an inner volume of 50 ml. The ruthenium metal content of the catalyst in the reaction mixture was adjusted to 0.5 ppm by weight. The reaction mixture containing the insoluble ruthenium complex suspended therein was heated at 120° C. for 30 minutes while stirring the reaction mixture, to decompose the cyclohexylhydroperoxide (CHP). After the reaction was completed, the resultant decomposition liquid was filtered to recover the catalyst, and the filtrate was subjected to and analyzed by gas chromatography.

As a result, it was confirmed that the CHP was completely decomposed. The KA yield was 109.1% and the K/A ratio (by mole) was 0.49.

EXAMPLE 2

The same air oxidation of cyclohexane and decomposition of cyclohexylhydroperoxide (CHP) as in Example 1 were carried out except that the catalyst recovered by filtration in Example 1 was employed.

The recovery of the catalyst and analysis of the reaction liquid was carried out in the same manner as in Example 1.

As a result, it was confirmed that CHP was completely decomposed. The KA yield was 109.5%, and the K/A ratio (by mole) was 0.49.

EXAMPLE 3

By the same procedures as in Example 1, cyclohexylhydroperoxide (CHP) was decomposed, the catalyst was recovered and the filtrate was analyzed, except that dichlorotris(triphenylphosphine)ruthenium was used in a ruthenium metal concentration of 0.1 ppm by weight, and the reaction time was changed to 60 minutes.

As a result, the CHP conversion was 99.0%, the KA yield was 107.1% and the K/A ratio (by mole) was 0.42. Also, it was found that in the reaction, the turn-over number of ruthenium was 130,000.

COMPARATIVE EXAMPLE 1

By the same procedures as in Example 1, the air oxidation of cyclohexane and the decomposition of cyclohexylhydroperoxide (CHP) were carried out, and the reaction liquid was analyzed, except that as a catalyst, soluble tris(acetylacetonato)ruthenium [Ru(acac)$_3$] was used, and the ruthenium metal concentration in the reaction liquid was adjusted to 0.5 ppm by weight.

As a result, the CHP conversion was 62.9%, the KA yield was 98.5%, and the K/A ratio (by mole) was 0.55. After the reaction was completed, it was found that a precipitate of the ruthenium compound was adhered to an inside wall surface of the reactor.

COMPARATIVE EXAMPLE 2

By the same procedures as in Example 1, the air oxidation of cyclohexane and the decomposition of cyclohexylhydroperoxide (CHP) were carried out, and the reaction liquid was analyzed, except that as a catalyst, soluble ruthenium trichloride [RuCl$_3$] was used, and the ruthenium metal concentration in the reaction liquid was adjusted to 0.5 ppm by weight.

As a result, the CHP conversion was 40.6%, the KA yield was 97.7%, and the K/A ratio (by mole) was 0.52.

Although a portion of the catalyst was dissolved in the reaction liquid, almost all of the catalyst was insolubilized (deactivated) and scaled on the inside wall surface of the reactor and thus could not be recovered.

The reaction conditions and reaction results of Examples 1 to 3 and Comparative Examples 1 and 2 are shown in Table 1.

TABLE 1

| Item Example No. | Reaction catalyst and reaction conditions | | | | Reaction results | | |
|---|---|---|---|---|---|---|---|
| | Ruthenium complex | Metal concentration (ppm by wt) | Reaction temperature (°C.) | Reaction time (min) | CHP conversion (%) | KA yield (%) | K/A molar ratio |
| Example | | | | | | | |
| 1 | [RuCl$_2$(PPh$_3$)$_3$] | 0.5 | 120 | 30 | 100 | 109.1 | 0.49 |
| 2 | [RuCl$_2$(PPh$_3$)$_3$] | 0.5 | 120 | 30 | 100 | 109.5 | 0.49 |
| 3 | [RuCl$_2$(PPh$_3$)$_3$] | 0.1 | 120 | 60 | 99.0 | 107.1 | 0.42 |
| Comparative Example | | | | | | | |
| 1 | [Ru(acac)$_3$] | 0.5 | 120 | 30 | 62.9 | 98.5 | 0.55 |
| 2 | [RuCl$_3$] | 0.5 | 120 | 30 | 40.6 | 97.7 | 0.52 |

Note:
1) PPh$_3$ ... triphenylphosphine
acac ... acetylacetonato
2) In Example 2, the catalyst used and recovered by filtering in Example 1 was reused.

EXAMPLES 4 TO 12

In each of Examples 4 to 12, the same procedures for oxidizing cyclohexane with air, decomposing cyclohexylhydroperoxide (CHP), recovering the catalyst and analyzing the reaction liquid as those in Example 1 were carried out, except that the type and concentration of the ruthenium complex used as a catalyst were as indicated in Table 2. The reaction results are shown in Table 2.

TABLE 2

| Item Example No. Example | Reaction catalyst and reaction conditions | | | | Reaction results | | |
|---|---|---|---|---|---|---|---|
| | Ruthenium complex | Metal concentration (ppm by wt) | Reaction temperature (°C.) | Reaction time (min) | CHP conversion (%) | KA yield (%) | K/A molar ratio |
| 4 | [RuCl$_2$(benzene)]$_2$ | 0.5 | 120 | 30 | 100 | 108.2 | 0.45 |
| 5 | [RuCl$_2$(p-cymene)]$_2$ | 0.5 | 120 | 30 | 100 | 116.8 | 0.49 |
| 6 | [RuCl$_2$(dmso)$_4$] | 0.5 | 120 | 30 | 100 | 123.7 | 0.63 |
| 7 | [RuCl$_2$(CH$_3$CN)$_4$] | 0.5 | 120 | 30 | 100 | 107.7 | 0.54 |
| 8 | [RuCl$_2$(C$_6$H$_5$CN)$_4$] | 0.5 | 120 | 30 | 100 | 107.0 | 0.52 |
| 9 | [RuCl$_2$(py)$_4$] | 0.5 | 120 | 30 | 100 | 110.2 | 0.57 |
| 10 | [RuCl$_2$(bpy)$_3$] | 0.5 | 120 | 30 | 100 | 112.6 | 0.57 |
| 11 | [RuCl$_2$(cod)]$_m$ | 0.5 | 120 | 30 | 100 | 105.5 | 0.45 |
| 12 | [RuCl$_2$(CH$_3$CN)$_2$(PPh$_3$)$_2$] | 0.5 | 120 | 30 | 100 | 108.9 | 0.56 |

Note:
1) PPh$_3$ ... triphenylphosphine
dmso ... dimethylsulfoxide
py ... pyridine
bpy ... 2,2'-bipyridine
cod ... 1,5-cyclooctadiene
acac ... acetylacetonato

EXAMPLE 13

[Oxidation of cyclodedecane with air]

Cyclododecane in an amount of 170 g was charged in the same pressure-resistant glass autoclave having an inner volume of 500 ml as in Example 1, and heated while stirring (800 rpm) and flowing nitrogen gas under a pressure of 10 kg/cm$^2$ at a flow rate of 50 l/hr through the autoclave. When the temperature reached 160° C., the nitrogen gas was replaced by air (pressure: 10 kg/cm$^2$, flow rate: 50 l/hr) to start an oxidation reaction.

At a stage of 46 minutes after the start of the reaction, the resultant oxidation reaction liquid was cooled. The oxidation reaction liquid contained, per g of the oxidation reaction liquid, 0.2534 millimole of cyclododecylhydroperoxide (CDHP), 0.1338 millimole of cyclododecanol and 0.1388 millimole of cyclododecanone.

[Decomposition of cyclododecylhydroperoxide]

The above-mentioned cyclododecane-oxidation reaction liquid in an amount of 10 g and a catalyst consisting of dichloro-tris(triphenylphosphine)ruthenium [RuCl$_2$(PPh$_3$)$_3$] were charged in a pressure-resistant glass autoclave having an inner volume of 100 ml similar to that in Example 1. The ruthenium metal content of the catalyst in the reaction mixture was adjusted to 0.5 ppm by weight. The reaction mixture containing the insoluble ruthenium complex suspended therein was heated at 140° C. for 60 minutes while stirring the reaction mixture, to decompose cyclododecylhydroperoxide (CDHP). After the reaction was completed, the resultant decomposition liquid was filtered to recover the catalyst, and the filtrate was subjected to and analyzed by gas chromatography.

As a result, it was confirmed that the CDHP was completely decomposed. When the same calculation as in Example 1 was carried out, the total yield of cyclododecanone and cyclododecanol was 116.1%, and the molar ratio of cyclododecanone to cyclododecanol was 0.75.

EXAMPLE 14

[Oxidation of cyclohexane with air]

Cyclohexane in an amount of 300 g and 1.4 g of a reaction-initiator consisting of t-butylhydroperoxide were charged in the same pressure-resistant glass autoclave having an inner volume of 500 ml as in Example 1, and heated while stirring (800 rpm) and flowing a nitrogen gas under pressure of 10 kg/cm$^2$ at a flow rate of 40 l/hr through the autoclave. When the temperature reached 160° C., the nitrogen gas was replaced by air (pressure: 10 kg/cm$^2$, flow rate: 40 l/hr) to start an oxidation reaction.

At a stage of 60 minutes after the start of the reaction, the resultant oxidation reaction liquid was cooled. The oxidation reaction liquid contained, per g of the oxidation reaction liquid, 0.307 millimole of cyclohexylhydroperoxide (CHP), 0.072 millimole of cyclohexanol (A) and 0.042 millimole of cyclohexanone (K).

[Decomposition of cyclohexylhydroperoxide]

The above-mentioned cyclohexane-oxidation reaction liquid in an amount of 85 g and a catalyst consisting of dichloro-tris(triphenylphosphine)ruthenium [RuCl$_2$(PPh$_3$)$_3$] were charged in a pressure-resistant glass autoclave equipped with a reflux condenser, a thermometer, a water separator, a gas inlet pipe, a stirrer and an outlet for withdrawing a reaction liquid and having an inner volume of 500 ml. The ruthenium metal content of the catalyst in the reaction mixture was adjusted to 0.5 ppm by weight. The reaction mixture containing the insoluble ruthenium complex suspended therein was heated at 120° C. for 30 minutes while stirring the reaction mixture, to decompose cyclohexylhydroperoxide (CHP). After the reaction was completed, the resultant decomposition liquid was filtered to recover the catalyst, and the filtrate was subjected to and analyzed by gas chromatography.

As a result, it was confirmed that the CHP was completely decomposed. The total yield (KA yield) of cyclohexanone and cyclohexanol was 109.1%, and the molar ratio of cyclohexanone to cyclohexanol (K/A) was 0.49.

The conversion of cyclohexane through both the oxidation step of cyclohexane and the decomposition step of CHP was 4.2%, and the total selectivity of cyclohexanone (K) and cyclohexanol (A) (percentage of the total amount both the compounds to all the products) was 89 molar %.

COMPARATIVE EXAMPLE 3

By the same procedures as in Example 14, the air oxidation of cyclohexane and the decomposition of cyclohexylhydroperoxide (CHP) were carried out, and the reaction liquid was analyzed, except that as a catalyst, soluble cobalt octylate was used in place of the ruthenium complex, the cobalt metal concentration in the reaction liquid was adjusted to 1.0 ppm by weight, the reaction temperature was 160° C. and the reaction time was 60 minutes.

As a result, although the complete decomposition of CHP was confirmed, the KA yield was 101.2%, and the K/A ratio (by mole) was 0.35. Also, although the conversion of cyclohexane was 4.4%, the total selectivity of cyclohexanone and cyclohexanol (percentage of the total yield of both the compounds to all the product) was 79 molar %.

After the reaction was completed, it was found that a precipitate of the cobalt compound was adhered to an inside wall surface of the reactor.

INDUSTRIAL APPLICABILITY

In accordance with the process of the present invention, a cycloalkanone and cycloalkanol can be produced from a cycloalkylhydroperoxide by using a small amount of a catalyst insoluble in the reaction system and having a high activity, at a high reaction rate, at a high turnover number, at a high yield and a high selectivity (a percentage of the amount of the target compounds to all the products).

Also, in the process of the present invention, since a catalyst insoluble in the reaction system is employed, it is possible to readily separate the catalyst from the reaction liquid, to prevent deactivation or loss of the catalyst due to the distillation and circulation of the reaction liquid, and to significantly enhance the productive efficiency of the cycloalkanone and cycloalkanol in the industrial production, particularly by a continuous reaction procedure.

We claim:

1. A process for producing a cycloalkanol and cycloalkanone, comprising decomposing a cycloalkylhydroperoxide by bringing it into contact with a ruthenium complex represented by the general formula (I):

in which formula (I), L represents a neutral ligand coordinate-bonded to a ruthenium atom, n represents an integer of 1 to 4 and m represents an integer of 1 or more.

2. The process as claimed in claim 1, wherein the cycloalkylhydroperoxide has a cycloalkyl group having 5 to 20 carbon atoms.

3. The process as claimed in claim 1, wherein in the formula (I), the neutral ligand represented by L is selected from tertiary arylphosphine compounds, arene compounds, diene compounds, nitrile compounds, pyridine compounds, 2,2'-bipyridine compounds, 1,10-phenanthroline compounds and dimethylsulfoxide compounds.

4. The process as claimed in claim 1, wherein the ruthenium complex of the formula (I) is selected from dichloro-tris(triphenylphosphine)ruthenium, dichloro-tris(tris(4-methylphenyl)phosphine)ruthenium, dichloro-tris(tris(4-chlorophenyl)phosphine)ruthenium, dichloro-tris(tris(4-fluorophenyl)phosphine)ruthenium, dichloro-tris(tris(4-methoxyphenyl)phosphine)ruthenium, tetrachloro-bis(η-benzene)diruthenium, tetrachloro-bis(η-toluene)diruthenium, tetrachloro-bis(η-xylene)diruthenium, tetrachloro-bis(η-mesitylene)diruthenium, tetrachloro-bis(η-anisole)diruthenium, tetrachloro-bis(η-cycloheptatriene)diruthenium, associations of dichloro(cyclooctadiene)ruthenium, associations of tetrachloro-bis(norbornadiene)ruthenium, dichloro-tetrakis(acetonitrile)ruthenium, dichloro-tetrakis(propionitrile)ruthenium, dichloro-tetrakis(butyronitrile)ruthenium, dichloro-tetrakis(benzonitrile)ruthenium, dichloro-tetra(pyridine)ruthenium, dichloro-tris(2,2'-bipyridine)ruthenium, dichloro-tris(4,4'-dimethyl-2,2'-bipyridine)ruthenium, dichloro-tris(1,10-phenanthroline)ruthenium, dichloro-bis(acetonitrile)bis(triphenylphosphine)ruthenium, and dichloro-tetrakis(dimethylsulfoxide)ruthenium.

5. The process as claimed in claim 1, wherein the ruthenium complex of the formula (I) is employed in an amount of 0.01 to 250 ppm by weight in terms of the weight of ruthenium metal, based on the total reaction system weight.

6. The process as claimed in claim 1, wherein the decomposing step is carried out at a temperature of 25 to 180° C. under a pressure of 1 to 30 atmospheres.

7. The process as claimed in claim 1, wherein the ruthenium complex of the formula (I) is isolated and recovered by filtering and reused.

* * * * *